United States Patent [19]

Feiring et al.

[11] Patent Number: 5,350,821

[45] Date of Patent: Sep. 27, 1994

[54] FLUORINATED MONOMERS AND POLYMERS

[75] Inventors: Andrew E. Feiring; Bruce E. Smart; Zhen-Yu Yang, all of Wilmington, Del.

[73] Assignee: E. I. Du Pont de Nemours and Company, Wilmington, Del.

[21] Appl. No.: 197,780

[22] Filed: Feb. 16, 1994

Related U.S. Application Data

[60] Division of Ser. No. 61,888, May 14, 1993, which is a continuation-in-part of Ser. No. 994,032, Dec. 21, 1992, Pat. No. 5,260,492.

[51] Int. Cl.$^5$ .................................................. C08F 16/24
[52] U.S. Cl. ...................................... 526/247; 526/249; 526/255
[58] Field of Search ....................... 526/247, 249, 255

[56] References Cited

U.S. PATENT DOCUMENTS 4,897,457  1/1990  Nakamura et al. .................. 526/247

OTHER PUBLICATIONS

J. E. Fearn, et al., *J. Polym. Sci. A1*, 4, 131–140, 1966.
D. W. Brown et al., *J. Polym. Sci. A-2*, 7, 601–608, 1969.

*Primary Examiner*—Joseph L. Schofer
*Assistant Examiner*—N. Sarofim

[57] ABSTRACT

Disclosed herein are novel monomers of the formula $CF_2=CF(CF_2)_nCH_2OCF=CF_2$, wherein n is 1, 2 or 3, and novel intermediates of the formula $CF_2ClCFCl(CF_2)_nCH_2OCF=CF_2$ wherein n is 1, 2 or 3. Also disclosed is a fluoro-polymer containing cyclic units when the monomer wherein n is 1 is free radically polymerized. The polymer is particularly useful in for coatings and encapsulants.

7 Claims, No Drawings

FLUORINATED MONOMERS AND POLYMERS

This is a divisional of Ser. No. 08/061,888, filed on May 14, 1993, which is a continuation-in-part of Ser. No. 07/994,032, filed on Dec. 21, 1992 now U.S. Pat. No. 5,260,492.

FIELD OF THE INVENTION

This invention concerns novel partially fluorinated alkenyl vinyl ether monomers which can be (co)polymerized to novel polymers containing ring structures which can be chlorinated. The polymers are useful for films and coatings. Also claimed are novel intermediates for making the monomers.

TECHNICAL BACKGROUND

The instant monomers, partially fluorinated omega-alkenyl vinyl ethers, can be polymerized to uncrosslinked (soluble), semicrystalline, polymers. In U.S. Pat. No. 4,897,457 it is reported that perfluorinated omega-alkenyl vinyl ethers can be polymerized to polymers that are amorphous and contain ring structures.

J. E. Fearn, et al., J. Polym. Sci. A-1, volume 4, p. 131–140 (1966) and D. W. Brown et al., J. Polym. Sci. A-2, vol. 7, p. 601–608 (1969) report that certain perfluorinated alpha-omega dienes can be polymerized to soluble ring containing polymers. These polymers are not reported to be crystalline.

SUMMARY OF THE INVENTION

This invention concerns a compound of the formula $CF_2=CF(CF_2)_nCH_2OCF=CF_2$, wherein n is 1, 2 or 3.

This invention also concerns a compound of the formula $CF_2ClCFCl(CF_2)_nCH_2OCF=CF_2$, wherein n is 1, 2 or 3.

This invention involves a polymer, comprising, the repeat unit(s)

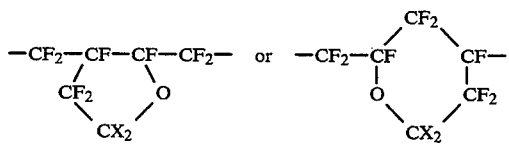

or both, and wherein both of X are hydrogen or chlorine.

DETAILS OF THE INVENTION

This invention concerns certain partially fluorinated omega-alkenyl vinyl ethers and polymers made by free radical polymerization. The polymers are semicrystalline with a high melting point, yet are soluble in selected common organic solvents and they may be chlorinated to give novel perhalo polymers. All of these polymers are particularly suited for films and coatings.

The omega-alkenyl vinyl ethers have the formula $CF_2=CF(CF_2)_nCH_2OCF=CF_2$, wherein n is 1, 2 or 3. When n is 1 or 3, this compound can be made by telomerizing 1,2-dichloroiodotrifluoroethane with tetrafluoroethylene (TFE). If one molecule of TFE is added to the iodo compound, the monomer where n is 1 results, while if two molecules of TFE are added to the iodo compound, the monomer where n is 3 will result [for a discussion of this reaction, see J. E. Fearn, J. Natl. Bureau Stds., Part A, vol. 75 p. 41–56 (1971)]. The resulting iodide is then reacted with oleum and mercuric oxide to form the corresponding acyl fluoride, which is reduced with LiAlH4 to the alcohol. The alkoxide of the alcohol is then formed by reaction with a strong base such as NaH, and the alkoxide is reacted with TFE to form vinyl ethers, which are the claimed intermediates $CF_2ClCFCl(CF_2)_nCH_2OCF=CF_2$, wherein n is 1 or 3. The omega-alkenyl double bond is then formed by dechlorination, as with zinc metal. See the Examples herein for further details. In preferred partially fluorinated omega-alkenyl vinyl ethers, and the claimed dichloro intermediates, it is preferred if n is 1.

The fluorinated alkenyl vinyl ether (monomer) where n is 2 can be made by reacting 1,2-dichloro-4-iodoperfluorobutane with ethylene to form 1,2-dichloro-1,1,2,3,3,4,4-heptafluoro-6-iodohexane, from which HI is eliminated to form 5,6-dichloro-3,3,4,4,5,6,6-heptafluoro-1-hexene. This olefin is then oxidized to 4,5-dichloro-2,2,3,3,4,5,5-heptafluoropentanoic acid, which is esterified, and then the ester is reduced to the alcohol, 4,5-dichloro-2,2,3,3,4,5,5,-heptafluoro-1pentanol. At this point the synthesis becomes similar to those for the fluorinated omega-alkenyl vinyl ethers where n is 1 or 3. For details of making the monomer where n is 2, see Examples 11–13.

The free radical (co)polymerization of the fluorinated omega-alkenyl vinyl ethers can be done by means known to those skilled in the art of fluoroolefin (including vinyl ethers) polymerization, see for instance U.S. Pat. No. 4,897,457 and H. F. Mark, et al., Ed., Encyclopedia of Polymer Science and Engineering, Vol. 16, John Wiley and Sons, N.Y., 1989, p. 577–648, both of which are hereby included by reference. Thus, the polymerization may be carried out neat, in solvent, or in nonaqueous suspension, aqueous suspension, or aqueous emulsion. Suitable free radical initiators include bis(perfluoropropionyl) peroxide and bis(4-t-butylcyclohexylperoxy) dicarbonate. Typical (co)polymerizations are described in Examples 8–10.

Suitable comonomers include fluorinated and unfluorinated monomers such as tetrafluoroethylene, hexafluoropropylene, vinylidene fluoride, perfluoro(methyl vinyl ether), perfluoro(propyl vinyl ether), methyl vinyl ether, propylene, ethylene, chlorotrifluoroethylene, perfluoro(2,2-dimethyl-1,3-dioxole), and $CF_2=CF(CF_2)_mOCF=CF_2$ where m is 1, 2 or 3. Preferred comonomers are tetrafluoroethylene and perfluoro(propyl vinyl ether). Also preferred are the homopolymers of the instant fluorinatedomega-alkenyl vinyl ethers. Preferred homopolymer and copolymers are also those in which n is 1 in the fluorinated omega-alkenyl vinyl ether monomer used (to give the corresponding polymer repeat unit.

By "comprising" herein in the claim to polymers containing the

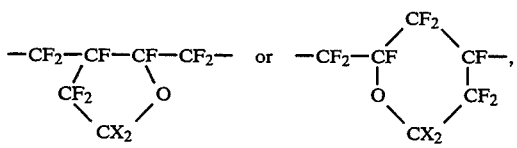

or both repeat units, is meant that the polymer contains this unit(s), and can optionally contain other units (from comonomers) .

The polymers made herein are useful in molding parts, and in coatings and encapsulants. When X is hydrogen they are particularly useful as coatings and encapsulants because even though they may have a high fluorine content, a high melting point, and good thermal stability, they are soluble in certain common organic solvents, such as ethyl acetate, acetone, diglyme, tetrahydrofuran and N,N-dimethylformamide. Solutions of the polymers may be used to coat or encapsulate articles in conventional ways.

When X is chlorine the polymers are more thermally stable and are soluble in (per)halogonated compounds such as carbon tetrachloride and 1,1,2-trichloro-1,2,2trifluoroethane (F-113).

Polymers where X is chlorine are made by chlorination of polymers where X is hydrogen. The chlorination is conveniently carried out by contacting the hydrogen containing polymer with chlorine, preferably in the presence of actinic radiation (e.g., the light from a sunlamp).

In the Examples, the following abbreviations are used:

DMF - N,N-dimethylformamide
GC - gas chromatography
GPC - gel permeation chromatography
Mw - weight average molecular weight
TFE - tetrafluoroethylene
TGA - thermogravimetric analysis

EXAMPLE 1

SYNTHESIS OF 3,4-DICHLORO-1-IODOPERFLUOROOBUTANE

A mixture of 400 g of 1,2-dichloro-1-iodotrifluoroethane, 140 g of tetrafluoroethene and 4 g of benzoyl peroxide was heated in 1L autoclave at 130° C. for 4.5 hours. GC analysis of the reaction mixture (458 g) indicated 37% of starting material, 51% of desired product and 7% of 5,6-dichloro-1-iodoperfluorohexane. The reaction mixture was distilled on a 91 cm spinning band column to give 18.6 g of lower boiler, bp 80°–99° C. (mainly starting material), 138.6 g of starting material, bp 100°–102° C., 50.1 g of mixture of starting material and desired product, bp 103°–140° C. and 211 g of pure desired product, bp 140°–142° C.

EXAMPLE 2

SYNTHESIS OF 3,4-DICHLOROPERFLUOROBUTYRYL FLUORIDE

A 1 L three-necked flask, fitted with a stir bar and condenser, was charged with 3.0 g of HgO (yellow), 25 mL of 20% oleum, 25 mL of 65% oleum and 75.6 g of 3,4-dichloro-1-iodoperfluorobutane. After the reaction mixture was heated at 110° C. for 2 hours, the condenser was replaced by a distillation head with a 250 mL flask for receiver cooled with ice water. Volatiles were collected, washed with 98% sulfuric acid to remove sulfur trioxide and redistilled to give 40.3 g of 3,4-dichloroperfluorobutyryl fluoride, bp 72°–75° C., 99.8% GC purity.

EXAMPLE 3

SYNTHESIS OF 1,1-DIHYDRO-2,2,3,4,4-PENTAFLUORO-3,4,-DICHLOROBUTANOL

A 1L three-necked flask fitted with a stir bar, a condenser and an addition funnel was charged with 74.4 g of 3,4-dichloroperfluorobutyryl fluoride and 500 mL of anhydrous ether. Lithium aluminum hydride in ether (1.0M, 160 mL) was added dropwise at −26° to −30° C. over one hour. After the addition was complete, the reaction mixture was stirred at −30° C. to room temperature for 3 hours, then quenched with water and 10% HCl. The ether layer was separated and aqueous layer was extracted with ether. The combined ether layers were washed with water and dried over MgSO$_4$. After evaporation of the ether, a residue was distilled to give 67.4 g of alcohol, bp 141°–151° C. Anal: Calcd for C$_4$H$_3$F$_5$Cl$_2$O: C, 20.61; H, 1.29; F, 40.79; Cl, 30.44. Found: C, 20.48; H, 1.37; F, 40.96; Cl, 29.74. GC analysis of this alcohol indicated two peaks in a 20:80 ratio. Redistillation on spinning band gave 138°–153° C. material and 153°–154° C. material. The latter exhibited only one peak in GC with 99.7% purity. $^{19}$F NMR(CDCl$_3$): −63.8 (m, 2F), −116.6 (m, 2F), −132.0 (m, 1F); $^1$H NMR(CDCl$_3$): 4.15 (td, J=14.7 Hz, J=7.3 Hz, 2H), 2.82 (br, 1H). IR(neat): 3360 (vs), 1215 (s), 1160 (s), 1110 (s), 1035 (s). Anal: Calcd for C$_4$H$_3$F$_5$Cl$_2$O: C, 20.61; H, 1.29; F, 40.79. Found: C, 20.86; H, 1.49; F, 40.48.

EXAMPLE 4

SYNTHESIS OF 1,1-DIHYDRO-2,2,3,4,4-PENTAFLUORO-3,4,-DICHLOROBUTYL TRIFLUOROVINYL ETHER

To a stirred solution of 5.2 g of NaH (80% NaH in mineral oil) and 150 mL of anhydrous ether was slowly added 27.8 of 3,4-dichloro-2,2,3,4,4-pentafluorobutanol at 0° C. over 30 minutes. After the addition was complete, the resulting mixture was stirred at 0° C. to room temperature for 1.5 hours, and then poured into a 300 mL shaker tube. The tube was purged with N$_2$ and pressured with TFE to 2.41 MPa to 2.76 MPa and then kept at 50° C. for 15 hours. The reaction mixture was quenched with 10 mL of methanol and poured into 50 mL of water. The ether layer was separated and aqueous layer was extracted with ether. The combined ether layers were dried over MgSO$_4$. After evaporation of the ether, a residue was distilled under reduced pressure to give 20.8 g of desired product, bp 74° C./73 mmHg. $^{19}$F NMR (CDCl$_3$): −63.7 to −64.0 (m, 2F), −115.0 (m, 2F), −121.3 (dd, J=98.5 Hz, J=59.1 Hz, 1F), −127.1 (dd, J=108.8 Hz, J=98.7 Hz, 1F), −131.8 (m, 1F), −137.8 (dd, J=108.6 Hz, J=59.1 Hz, 1F); $^1$H NMR (CDCl$_3$): 4.47 (t, J=14.0 Hz). HRMS: Calcd for C$_6$H$_2$F$_8$Cl$_2$O: 311.9355. Found: 311.9321.

EXAMPLE 5

SYNTHESIS OF 1,1-DIHYDRO-2,2,3,4,4-PENTAFLUORO-3-BUTENYL TRIFLUOROVINYLETHER (DPBTVE)

A two-necked flask fitted with a stir bar and a condenser topped with a nitrogen inlet was charged with 3.5 g of acid-washed zinc powder and 15 mL of anhydrous DMF. After the mixture was heated to 90° C., 1.0 g of 1,2-dibromoethane was slowly added and then stirred an additional 10 minutes. 1,1-Dihydro-2,2,3,4,4-pentafluoro-3,4-dichlorobutyl trifluorovinyl ether (7.0 g) was slowly added by means of syringe over 30 minutes and the resulting mixture was stirred for 1.5 hours. The condenser was replaced with distillation head and 3.85 g of volatile material were collected in dry ice-acetone trap under partial vacuum (200 mmHg). Redistillation gave 3.50 g of desired product, bp 84°–85° C., 99.0% GC purity. $^1$H NMR (CDCl$_3$): 4.32 (t, J=11.3 Hz); $^{19}$F NMR(CDCl$_3$): −91.9 (ddt, J=57.7 Hz, J=36.6 Hz, J=5.4 Hz, 1F), −107.9 (ddt, J=115.7 Hz, J=57.8 Hz, J=31.1 Hz, 1F), −111.3 (m, 2F), −121.5 (dd, J=99.4 Hz, J=59.0 Hz, 1F), −127.8 (dd, J=109.0 Hz, J=99.5 Hz, 1F), −137.4 (dd, J=109.0 Hz, J=59.0 Hz, 1F), −190.2 (ddt, J=115.5 Hz, J=36.7 Hz, J=14.7 Hz, 1F). IR(neat): 2980 (w), 1845 (w), 1790 (vs), 1320 (m), 1175 (vs), 1040 (v). Anal: Calcd. for $C_6H_2F_8O$: C, 29.75; H, 0.83. Found: C, 30.15; H, 0.85.

EXAMPLE 6

POLYMERIZATION OF 1,1-DIHYDRO-2,2,3,4,4-PENTAFLUORO-3-BUTENYL TRIFLUOROVINYLETHER INITIATED WITH BIS (PERFLUOROPROPIONYL) PEROXIDE

A 25 mL glass ampul fitted with a Teflon ® (registered Tradmark E. I. du Pont de Nemours and Company) coated stir bar was charged with 13.5 mg of bis (perfluoropropionyl) peroxide in 0.18 ml of 1,1,2-trichlorotrifluoroethane and 1.0 g of the title compound. The ampul was sealed and cooled in a liquid nitrogen bath. After being evacuated and purged with Ar gas alternately six times, contents of the sealed ampul were stirred at 45° to 50° C. for 15 hours. The resulting white solids were dissolved in ethyl acetate, reprecipitated by addition of methanol and dried under vacuum at 85° C. to give 0.90 g of polymer.

The IR spectrum of this polymer shows no absorption at around 1790 cm$^{-1}$ which could be attributed to double bonds in the polymer. $^1$H NMR and $^{19}$F NMR analysis of this polymer in acetone-d$_6$ indicates the cyclic structure. $^1$H NMR (vs. TMS): 5.2–4.8 (br); $^{19}$F NMR (vs. CFCl$_3$): −112.5 to −122.0 (m, 7F), −178.0 to −183.0 (m, 1F).

This polymer is soluble in acetone, ethyl acetate, diglyme, tetrahydrofuran and dimethylformamide, and is insoluble in 1,1,2-trichlorotrifluoroethane, chloroform, toluene and methanol. The polymer has a glass transition temperature at 126.9° C. with melting point 347° C. The inherent viscosity of this material in DMF at 25° C. is 0.945 dl/g and could be obtained as a colorless and transparent thin film upon removing solvent from its solution in DMF spread on a glass plate. GPC analysis indicates that $M_w$ is 404000 and $M_n$ is 190000. By TGA the polymer shows 10% weight loss temperatures of about 485° C. under nitrogen and 360° C. under air, respectively, when heated at 20° C./minute.

EXAMPLE 7

POLYMERIZATION OF 1,1-DIHYDRO-2,2,3,4,4-PENTAFLUORO-3-BUTENYL TRIFLUOROVINYLETHER (DPBTVE) INITIATED WITH DI (4-T-BUTYLCYCLOHEXYL PEROXY) DICARBONATE

A 25 mL glass ampul fitted with a Teflon ® coated stir bar was charged with 20 mg of di(4-t-butylcyclohexylperoxy) dicarbonate and 1.17 g of DPBTVE. The ampul was sealed and cooled in a liquid nitrogen bath. After being evacuated and purged with Ar gas alternately six times, contents of the sealed ampul were stirred at 45° to 50° C. for 2 hours. Polymer (1.02 g) was obtained.

This polymer is soluble in acetone, ethyl acetate, diglyme, tetrahydrofuran and dimethylformamide, and is insoluble in 1,1,2-trichlorotrifluoroethane, chloroform, toluene and methanol. The polymer has a glass transition temperature at 120.4° C. with melting point 356.4° C. By TGA the polymer shows 10% weight loss temperatures of about 480° C. under nitrogen and 370° C. under air, respectively, when heated at 20° C./minute.

EXAMPLE 8

COPOLYMERIZATION OF DPBTVE WITH PERFLUOROPHORYL VINYL ETHER (PPVE)

A 25 mL glass ampul fitted with a Teflon ® coated stir bar was charged with 20 mg of di(4-t-butylcyclohexyl peroxy) dicarbonate, 1.0 g of DPBTVE and 0.5 g of PPVE. The ampul was sealed and cooled in a liquid nitrogen bath. After being evacuated and purged with Ar gas alternately six times, contents of the sealed ampul were stirred at 40° C. overnight. The resulting white solids were dissolved in ethyl acetate, reprecipitated by addition of methanol and dried under vacuum at 100° C. to give 0.93 g of polymer. This polymer was dissolved in acetone-d$_6$ to measure its $^{19}$F NMR spectrum, from which the polymer was found to be a copolymer consisting of units of the cyclic structure derived from DPBTVE and units of the structure derived from PPVE in a 88 to 12 ratio.

The polymer has a glass transition temperature at 100° C. with melting point 301° C. GPC analysis indicates that $M_w$ is 71200 and $M_n$ is 18100. By TGA the polymer shows 10% weight loss temperatures of about 470° C. under nitrogen and 350° C. under air, respectively, when heated at 20° C./minute.

EXAMPLE 9

COPOLYMERIZATION OF DPBTVE WITH PERFLUORO-(2,2-DIMETHYL-1,3-DIOXOLE (PDD)

A 25 mL glass ampul fitted with a Teflon ® coated stir bar was charged with 20 mg of di(4-t-butylcyclohexylperoxy) dicarbonate, 0.8 g of DPBTVE and 0.5 g of PDD. The ampul was sealed and cooled in a liquid nitrogen bath. After being evacuated and purged with Ar gas alternately six times, contents of the sealed ampul were stirred at 40° C. overnight. The resulting white solids were dissolved in 10 mL of ethyl acetate; no precipitation was observed by addition of 8 mL of methanol. Evaporation of the solvents gave colorless and transparent solids, which were dried under vacuum at 100° C. overnight to give 0.95 g polymer. This polymer was dissolved in acetone-d$_6$ to measure its $^{19}$F NMR spectrum, from which the polymer was found to be a copolymer consisting of units of the cyclic structure derived from DPBTVE and units of the structure derived from PDD in a 90 to 10 ratio.

The polymer has a glass transition temperature at 106.5° C. with melting point 341.2° C. GPC analysis indicates that $M_w$ is 74100 and $M_n$ is 19200. By TGA the polymer shows 10% weight loss temperatures of about 460° C. under nitrogen and 360° C. under air, respectively, when heated at 20° C./minute.

EXAMPLE 10

COPOLYMERIZATION OF DPBTVE WITH 3,4-DICHLORO-2,2,3,4,4-PENTAFLUOROBUTYL TRIFLUOROVINYL ETHER

A 25 mL glass ampul fitted with a Teflon ® coated stir bar was charged with 20 mg of di(4-t-butylcyclohexylperoxy) dicarbonate, 0.6 g of DPBTVE and 0.4 g of 3,4-dichloro-2,2,3,4,4-pentafluorobutyl trifluorovinyl ether. The ampul was sealed and cooled in a liquid nitrogen bath. After being evacuated and purged with Ar gas alternately six times, contents of the sealed ampul were stirred at 40° C. overnight. The formed colorless and transparent solids were dissolved in 10 mL of ethyl acetate; no precipitation was observed by addition of 8 mL of methanol. After evaporation of the solvents, the residue was dried under vacuum at 80° C. for 4 hours to give 0.90 g polymer. This polymer was dissolved in acetone-$d_6$ to measure its $^{19}F$ NMR spectrum, from which the polymer was found to be a copolymer consisting of a unit of the cyclic structure derived from 1 and a unit of the structure derived from 3,4-dichloro-2,2,3,4,4-pentafluorobutyl trifluorovinyl ether in a 87 to 13 ratio.

The polymer has a glass transition temperature at 79.9° C. GPC analysis indicates that $M_w$ is 74100 and $M_n$ is 19200. By TGA the polymer shows 10% weight loss temperatures of about 300° C. under nitrogen and 360° C. under air, respectively, when heated at 20° C./minute.

EXAMPLE 11

SYNTHESIS OF 5,6-DICHLORO-3,3,4,4,5,6,6-HEPTAFLUORO-1-HEXENE

A mixture of 417 g of 1,2-dichloro-4-iodoperfluorobutane and 62 g of ethylene was heated at 210°–220° C. in autoclave for 8 hours. After the reaction mixture was washed with $Na_2S_2O_3$ solution, 1,2-dichloro-1,1,2,3,3,4,4,-heptafluoro-6-iodohexane (434.6 g, 96.6% pure) was obtained. $^{19}F$ NMR: −64.0 (m, 2F), −112.9 (m, 2F), −116.0 (m, 2F), −131.0 (m, 1F). $^1H$ NMR: 3.25 (t, J=7.7 Hz, 2H), 2.64–2.82 (m, 2H).

To a stirred solution of 1,2-dichloro-1,1,2,3,3,4,4,-heptafluoro-6-iodohexane (370.0 g) and ethanol (400 mL) was added dropwise a solution of potassium hydroxide (56.0 g), ethanol (300 mL) and water (20 mL) at 80°–90° C. over 40 minutes. After the addition was complete, the reaction mixture was refluxed for 1 hour and then poured into water. Lower layer was separated and washed with water to give desired product (233.5 g). $^{19}F$ NMR: −63.9 (m, 2F), −111.9 (m, 2F), −116.2 (m, 2F), −130.5 (m, 1F); $^1H$ NMR: 5.72 to 6.10 (m). IR: 1651 (m), 1422 (s), 1180 (s), 1055 (s), 1019 (s), 1002 (s), 980 (s).

EXAMPLE 12

SYNTHESIS OF 4,5-DICHLORO-2,2,3,3,4,5,5-THEPTAFLUOROPENTANOL

To a stirred solution of $KMnO_4$ (64 g), KOH (11.2 g) and water (150 mL) was slowly added 5,6-dichloro-3,3,4,4,5,6,6-heptafluoro-1-hexene at 100° C. After the addition was complete, the resulting mixture was stirred at 100° C. for 3 hours and then cooled to room temperature. After being treated with sulfur dioxide, the mixture was acidified with 40% $H_2SO_4$ and extracted with ether. The ether layer was dried over $MgSO_4$. Evaporation of the ether gave the residue which was distilled to give 4,5-dichloro-2,2,3,3,4,5,5-heptafluoropetanoic acid (22 g), bp 99°–100° C./11 mmHg.

The above acid was stirred with ethanol (65 g) and conc. $H_2SO_4$ (1 mL) at 80° C. overnight, and then poured to water. Lower layer was separated and washed with water to give the corresponding ester (19.8 g). $^{19}F$ NMR: −64.0 (m, 2F), −115.7 (m, 2F), −116.5 (m, 2F), −131.3 (m, 1F); $^1H$ NMR: 4.43 (q, J=7.2 Hz, 2H), 1.39 (t, J=7.2 Hz, 3H).

To a stirred solution of $NaBH_4$ (1.5 g) and ethanol (50 mL) was slowly added the above ester (19.6 g) at 10° C. and the resulting mixture was stirred at room temperature for 2 hours, and then quenched with 20% HCl. After most of the ethanol was evaporated, the residue was poured into water. Lower layer was separated and aqueous layer was extracted with ether. The combined organic layers were dried over $MgSO_4$. After evaporation of the ether, the residue was distilled to give desired alcohol (13.7 g), bp 81°–82° C./30 mmHg. $^{19}F$ NMR: 64.9 (m, 2F), −116.3 (m, 2F), −120.6 (m, 2F), −131.5 (m, 1F); $^1H$ NMR: 4.08 (t, J=14.2 Hz, 2H), 3.01 (br, 1H); IR: 3374 (s), 2958 (s), 1182 (s), 1089 (s), 1039 (s), 953 (s). Anal: Calcd for $C_5H_3F_7Cl_2O$: C, 21.21; H, 1.06; F, 47.01; Cl, 25.06. Found: C, 21.26; H, 1.08; F, 47.25; Cl, 24.67.

EXAMPLE 13

SYNTHESIS OF 1,1-DIHYDROPERFLUORO-4-PENTENYL TRIFLUOROVINYL ETHER

To a stirred solution of NaH (2.84 g, 60%) and dioxane (70 mL) was slowly added 4,5-dichloro-2,2,3,3,4,5,5-heptafluoro-1-pentanol (17.5 g) at room temperature. After the addition was complete, the resulting mixture was stirred at room temperature overnight. The mixture was transferred into a shaker tube and heated at 70° C. for one hour, and then cooled to −8° C. The tube was evacuated and pressured with TFE to 350 psi and then kept at 35° C. for 40 hours. The reaction mixture was transferred into a flask and distilled under vacuum. A mixture of products and dioxane was collected in dry ice-acetone cooled receiver, followed by treatment with zinc at 90° C. for 7 hours and then distillation. The distillate was poured into water and the mixture separated to give two layers. The lower layer was recovered and washed with water to give 2.5 g of materials of desired product and 1,1-dihydroperfluoro-4-pentenyl 2-chloroperfluoroethyl ether in a 40:57 ratio. GC-HRMS: Calcd for $C_7H_2F_{10}O$: 291.9946. Found: 291.9972; Calcd for $C_7H_2F_{11}ClO$: 354.9619. Found: 345.9451.

EXAMPLE 14

COPOLYMERIZATION OF 1,1-DIHYDROPENTAFLUORO-1-BUTENYL TRIFLUOROVINYL ETHER AND CHLOROTRIFLUOROETHENE (CTFE)

A 25 mL glass ampul fitted with a Teflon ® coated stir bar was charged with 0.2 mL of 5% bis(perfluoropropeonyl)peroxide in F113 and 1.20 g of DPBTVE. The ampul was sealed and cooled in a liquid nitrogen bath. After being evacuated and purged with $N_2$ gas alternately 4 times, 0.5 mL (0.7 g) of CTFE was transfered into the ampul which was cooled at liquid nitrogen, and then the ampul was sealed. The contents of the sealed ampul were stirred at 40 ° C. overnight. The resulting white solid was dissolved in 4 mL of ethyl acetate and no precipitation (only a little white cloudiness) was observed-upon addition 100 mL of methanol at room temperature. When cooled to 0° C., the solution became very clear. However, after the solution was warmed up to 50° C., white solids were precipitated, which were filtered, dried under vacuum at 120° C. to give 0.4 g polymer. After removal of solvent from the mother liquid, 0.3 g of polymer were obtained. The polymer was dissolved in acetone-d6 to measure its $^{19}$F NMR spectrum, from which the polymer was found to be a copolymer consisting of a unit of the cyclic structure derived from DPBTVE and a unit of the structure derived from CTFE in a 47.7 to 52.3 mol ratio.

The polymer had a glass transition temperature of 105.7° C. and no Tm. GPC analysis indicates that $M_w$ was 229000 and $M_n$ was 108000 (P/D=2.12). By TGA the polymer showed a 10% weight loss temperatures of about 440° C. under nitrogen and 33520 C. under air, respectively, when heated at 20° C./minute. A flexible and strong transparent thin film was obtained upon removing solvent from its solution in acetone spread on a glass plate.

EXAMPLE 15

Chlorine gas was slowly condensed into a mixture of 0.4 g of the polymer of Example 5 in 3.0 g of Fluorolube ® through a dry ice/acetone condenser connected to an N$_2$ inlet. After being stirred at 120° to 140° C. under sun lamp irradiation for 14 hours, the reaction mixture was diluted with F113 and precipitated by addition of acetone. White solids were collected by filtration, and then redissolved in F113. After addition of acetone, solids were flitrated and dried under vacuum at 110° C. to give 0.27 g of chlorinated polymer. $^1$H NMR(F113) indicated no proton and IR(KBr) indicated C-Cl bands at 775, 730 and 685 cm$^{-1}$. The polymer has its glass transition temperatures at 155° and 82° C. with small heat capacity. By TGA the polymer showed a 10% weight loss at a temperature of about 400° C. in either air or N$_2$ when heated at 20° C./min.

EXAMPLE 16

Chlorine gas was slowly condensed into a mixture of 0.50 g of the polymer of Example 8, and 3.5 g of Fluorolube ® through a dry ice/acetone condenser connected to an N$_2$ inlet. After being stirred at 120° to 140° C. under sun lamp irradiation for 14 hours, the reaction mixture was diluted with F113 and precipitated by addition of acetone. White solid (0.53 g) was collected by filtration and dried under vacuum at 100° C. This polymer was soluble in F113, CF$_2$ClCFClCF$_2$CFCl$_2$ and CCl$_4$, but insoluble in CHCl$_3$, DMF, acetone. $^1$H NMR(F113) indicated no proton. The polymer had a glass transition temperature of 131° C. By TGA the polymer showed a 10% weight loss at a temperature of about 415° C. in either air or N$_2$, when heated at 20 °C./min.

EXAMPLE 17

Chlorine gas was slowly condensed into a mixture of the polymer of Example 14 and 3.0 g of Fluorolube ® through a dry ice/acetone condenser connected to an N$_2$ inlet. After being stirred at 120° to 130 °C. under sun lamp irradiation for 14 hours, the reaction mixture was diluted with F113 and precipitated by addition of acetone. White solid (0.20 g) was collected by filtration and dried under vacuum at 110° C. The polymer had a glass transition temperature of 128° C. By TGA the polymer showed a 10% weight loss temperature of about 412° C. in air and 420° C. in N$_2$, respectively, when heated at 20° C./min.

What is claimed is:

1. A polymer comprising the repeat unit(s)

or both, where both of X are hydrogen or chlorine.

2. The polymer of claim 1 which is a homopolymer.
3. The polymer of claim 2 which is a copolymer.
4. The polymer of claim 3 wherein a comonomer is one or more of tetrafluoroethylene, hexafluoropropylene, vinylidene fluoride, perfluoro(methyl vinyl ether), perfluoro(propyl vinyl ether), methyl vinyl ether, propylene, ethylene, chlorotrifluoroethylene, perfluoro(2,2-dimethyl-1,3-dioxole), or CF$_2$=CF(CF$_2$)$_m$OCF=CF$_2$ where m is 1, 2 or 3.
5. The polymer of claim 4 wherein said comonomer is tetrafluoroethylene or perfluoro(propyl vinyl ether).
6. The polymer of claim 1 wherein X is hydrogen.
7. The polymer of claim 1 wherein X is chlorine.

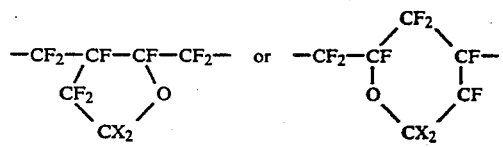

* * * * *